(12) United States Patent
Gabriel (10) Patent No.: US 11,259,954 B2
(45) Date of Patent: Mar. 1, 2022

(54) CONDOM CATHETERS AND METHODS OF MAKING AND USING THE SAME

(71) Applicant: Sabry Gabriel, Lizella, GA (US)

(72) Inventor: Sabry Gabriel, Lizella, GA (US)

( * ) Notice: Subject to any disclaimer, the term of this patent is extended or adjusted under 35 U.S.C. 154(b) by 607 days.

(21) Appl. No.: 16/132,578

(22) Filed: Sep. 17, 2018

(65) Prior Publication Data

US 2019/0091059 A1 Mar. 28, 2019

Related U.S. Application Data

(60) Provisional application No. 62/564,503, filed on Sep. 28, 2017.

(51) Int. Cl.
*A61F 5/443* (2006.01)
*A61F 5/44* (2006.01)
*A61F 5/453* (2006.01)

(52) U.S. Cl.
CPC ............ *A61F 5/443* (2013.01); *A61F 5/4405* (2013.01); *A61F 5/4408* (2013.01); *A61F 5/453* (2013.01)

(58) Field of Classification Search
CPC .......... A61F 5/453; A61F 5/442; A61F 5/451; A61F 6/04; A61F 6/041; A61F 6/06; A61F 6/065; A61B 10/007; A61M 2202/0496
See application file for complete search history.

(56) References Cited

U.S. PATENT DOCUMENTS

| | | | | |
|---|---|---|---|---|
| 3,511,241 A * | 5/1970 | Lee | ......................... | A61F 5/453 604/352 |
| 3,631,857 A * | 1/1972 | Maddison | ............... | A61F 5/453 604/349 |
| 3,742,953 A * | 7/1973 | Lee | ......................... | A61F 5/453 604/352 |
| 3,863,638 A * | 2/1975 | Rogers, III | ............. | A61F 5/453 604/352 |
| 4,656,675 A * | 4/1987 | Fajnsztajn | ............... | A61F 5/453 4/144.3 |
| 4,685,913 A * | 8/1987 | Austin | ..................... | A61F 5/453 604/349 |
| 4,790,834 A * | 12/1988 | Austin | ..................... | A61F 5/453 600/580 |
| 5,380,312 A * | 1/1995 | Goulter | ................... | A61F 5/453 604/352 |
| 5,707,341 A * | 1/1998 | Mathewuse | ............... | A61F 5/41 600/39 |
| 6,007,526 A * | 12/1999 | Passalaqua | ............. | A61F 5/453 128/844 |
| 2004/0006321 A1 * | 1/2004 | Cheng | ....................... | A61F 5/44 604/349 |
| 2005/0010181 A1 * | 1/2005 | Dolan | ..................... | A61F 5/453 604/351 |
| 2006/0004332 A1 * | 1/2006 | Marx | ....................... | A61F 5/453 604/349 |
| 2006/0069357 A1 * | 3/2006 | Marasco | ................. | A61M 1/90 604/289 |
| 2009/0259206 A1 * | 10/2009 | Kai | ........................... | A61F 5/44 604/352 |
| 2011/0022011 A1 * | 1/2011 | Edward | ................. | A61M 3/027 604/319 |

(Continued)

FOREIGN PATENT DOCUMENTS

CA 2083755 C * 2/2006 ............. A61F 5/453

*Primary Examiner* — Adam Marcetich
(74) *Attorney, Agent, or Firm* — Withers & Keys, LLC (57) ABSTRACT

Condom catheters and condom catheter systems containing a condom catheter are disclosed. The condom catheter systems utilize suction to attach a condom catheter to a patient's penis. Methods of making and using condom catheters are also disclosed.

19 Claims, 9 Drawing Sheets

(56) References Cited

U.S. PATENT DOCUMENTS

| | | | |
|---|---|---|---|
| 2013/0190708 A1* | 7/2013 | Rodsten | A61F 5/453 604/349 |
| 2013/0338617 A1* | 12/2013 | Newton, Jr. | A61F 5/453 604/353 |
| 2014/0249648 A1* | 9/2014 | Sandahl | A61F 2/68 623/32 |
| 2017/0007441 A1* | 1/2017 | Pascale | A61G 9/006 |
| 2017/0049608 A1* | 2/2017 | Chiaokun | A61F 6/04 |
| 2017/0340475 A1* | 11/2017 | Joh | A61F 5/4407 |

* cited by examiner

CONDOM CATHETERS AND METHODS OF MAKING AND USING THE SAME

CROSS-REFERENCE TO RELATED APPLICATIONS

This patent application claims the benefit of priority to U.S. Provisional Patent Application Ser. No. 62/564,503 filed on Sep. 28, 2017 and entitled "CONDOM CATHETERS AND METHODS OF MAKING AND USING THE SAME," the subject matter of which is hereby incorporated by reference in its entirety.

FIELD OF THE INVENTION

The present invention relates generally to condom catheters. The present invention further relates to devices and systems for securing condom catheters to a patient.

BACKGROUND OF THE INVENTION

Indwelling urinary catheters are catheters inserted through the penile urethra into the urinary bladder. They are frequently the cause for urinary tract infections (UTI). Alternatives to indwelling catheters are condom catheters. The main problem with condom catheters is that they leak around the penis or fall out.

Several mechanisms have been developed to secure condom catheters to the penis such as (i) adhesives on the inner surface of the condom to secure the condom catheter to the outer surface of the penis, and (ii) elastic materials such as silicon and various shapes and forms of belts and straps. So far, in clinical practice, none of the currently available devices and systems are successful in preventing leaks or condom separation from the penis.

Efforts continue to further develop useful condom catheters and condom catheter systems containing a condom catheter, as well as methods of effectively securing condom catheters to a patient.

SUMMARY OF THE INVENTION

The object of this invention is to provide a unique design of a condom catheter that utilizes low-pressure suction to secure the condom catheter to the outer surface of the penis, preventing leakage and detachment. A vacuum, or negative pressure suction, is applied between the inner surface of the condom catheter proximal part and the shaft of the penis allowing firm adhesion of the condom catheter to the penis's shaft while the distal penile urethral opening of the condom catheter is allowed to drain freely into common urinary closed collection bag systems by gravity or suction.

The condom catheters of the present invention may comprise a cylindrical tubular shape with a smaller distal opening, a larger proximal opening, and a component that enables the creation of a vacuum seal between the penis shaft and inner surface of the condom catheter. For example, in some embodiments, a vacuum system within an operating room setting, hospital room, ICU, nursing home or patient's home may be connected to a side port of the condom catheter so as to create suction that attaches the condom catheter to a patient's penis. In other embodiments, a syringe and a one way valve or shut off valve may be used to create the suction needed so as to attach the condom catheter to a patient's penis.

In one exemplary embodiment of the present invention, the condom catheter comprises a cylindrical tubular member sized to extend over a patient's penis and having a first tubular member end, a second tubular member end opposite the first tubular member end, a tubular member outer surface extending between the first tubular member end and the second tubular member end, a tubular member inner surface extending between the first tubular member end and the second tubular member end, a first opening at the first tubular member end, a second opening at the second tubular member end, a tubular member channel extending along the tubular member inner surface from the first tubular member end to the second tubular member end; and a side wall port positioned along the tubular member, the side wall port having a first side port end proximate the tubular member outer surface, a second side port end opposite the first side port end, a side port outer surface extending between the first side port end and the second side port end, a side port inner surface extending between the first side port end and the second side port end, a first side port opening at the first side port end along the tubular member inner surface, a second side port opening at the second side port end, and a side port channel extending along the side port inner surface extending between the first side port end and the second side port end so as to provide fluid communication between the second side port opening and the tubular member channel.

The present invention is also directed to kits comprising the condom catheters of the present invention. In one exemplary embodiment of the present invention, the kit comprises: at least one of the herein-described condom catheters of the present invention, and one or more additional kit components. Suitable additional kit components may include, but are not limited to, an open cell sponge ring, a distal end sponge insert or end piece, plastic tubing sized to connect to said side wall port or any other port/opening of the condom catheter, a syringe, a valve, a clamp, a suction-providing system, or any combination thereof.

The present invention is further directed to methods of making condom catheters. In one exemplary embodiment of the present invention, the method of making a condom catheter comprises: forming the tubular member and the side wall port of the herein-described condom catheters of the present invention. In some embodiments, the tubular member and the side wall port are integrally formed with one another. Further, in some embodiments, the forming step comprises a thermoforming step (e.g., a molding step).

The present invention is even further directed to methods of using a condom catheters. In one exemplary embodiment of the present invention, the method of using a condom catheter comprises a method of securing the condom catheter onto a patient comprising: positioning one of the herein-described condom catheters on a patient; and applying suction through the side wall port so as to increase a bonding strength between the condom catheter and the patient.

Other features and advantages of the present invention will become apparent after a review of the following detailed description of the disclosed embodiments and the appended claims.

BRIEF DESCRIPTION OF THE FIGURES

The present invention is further described with reference to the appended figures, wherein.

DETAILED DESCRIPTION OF THE INVENTION

The present invention is directed to condom catheters. The present invention is further directed to methods of making, as well as methods of using condom catheters.

Figure 1:
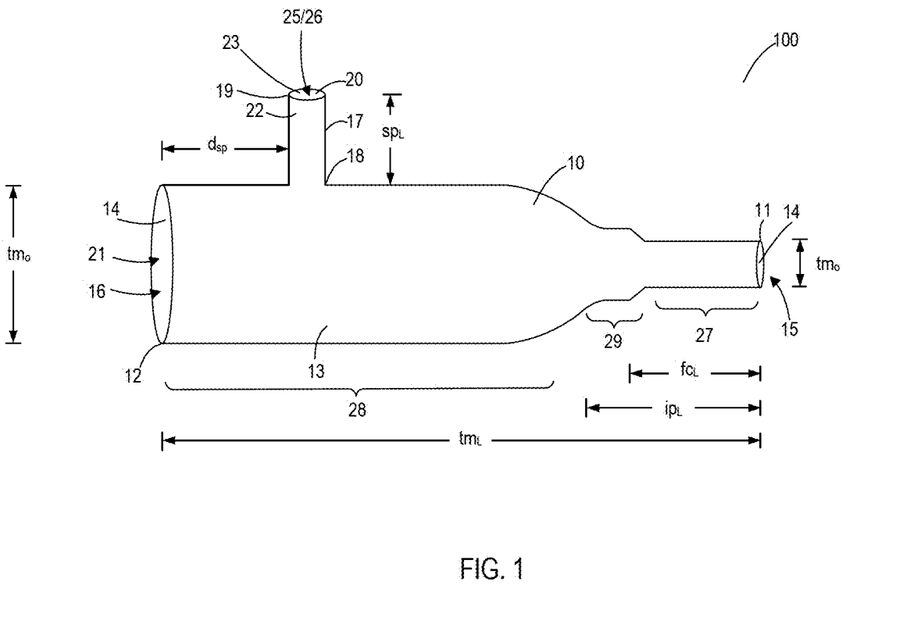
FIG. 1 depicts a view of an exemplary condom catheter of the present invention.
Figure 2:
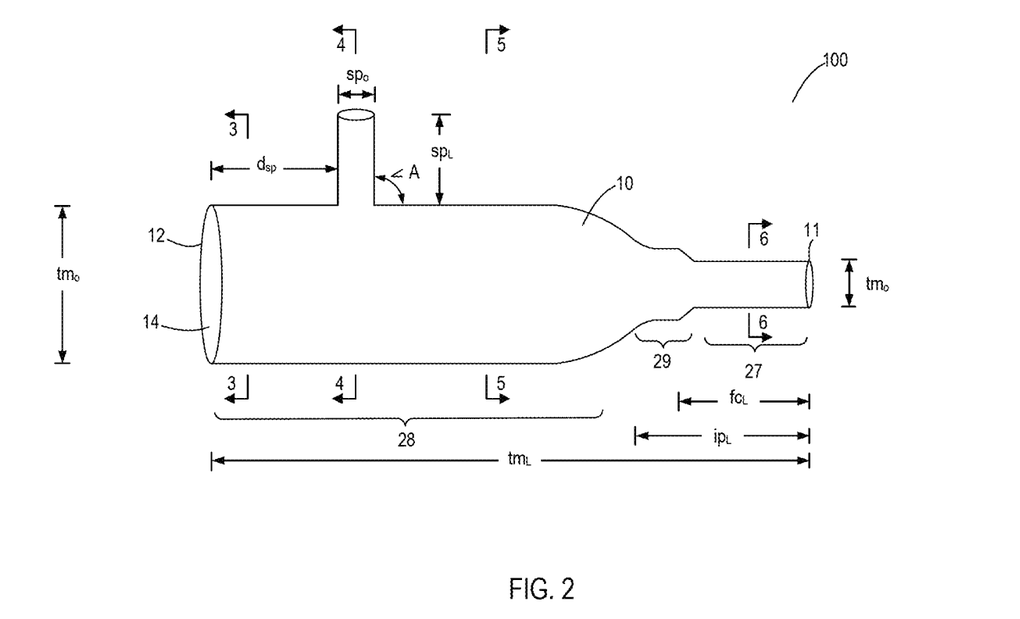
FIG. 2 depicts another view of an exemplary condom catheter of the present invention.

One exemplary condom catheter of the present invention is shown in FIG. 1. As shown in FIG. 1, exemplary condom catheter 100 comprising: a tubular member 10 sized to extend over a patient's penis (not shown) and having a first tubular member end 11, a second tubular member end 12 opposite said first tubular member end 11, a tubular member outer surface 13 extending between said first tubular member end 11 and said second tubular member end 12, a tubular member inner surface 14 extending between said first tubular member end 11 and said second tubular member end 12, a first opening 15 at said first tubular member end 11, a second opening 16 at said second tubular member end 12, a tubular member channel 21 extending along said tubular member inner surface 14 from said first tubular member end 11 to said second tubular member end 12, and a side wall port 17 positioned along said tubular member 10, said side wall port 17 having a first side port end 18 proximate said tubular member outer surface 13, a second side port end 19 opposite said first side port end 18, a side port outer surface 22 extending between said first side port end 18 and said second side port end 19, a side port inner surface 23 extending between said first side port end 18 and said second side port end 19, a first side port opening 24 at said first side port end 18 along said tubular member inner surface 14, a second side port opening 25 at said second side port end 19, and a side port channel 26 extending along said side port inner surface 23 extending between said first side port end 18 and said second side port end 19 so as to provide fluid communication between second side port opening 25 and tubular member channel 21.

Further additional embodiments of the present invention are described below. It should be noted that the recitation of numerical ranges by endpoints in any of the embodiments disclosed herein includes all numbers subsumed within that range (e.g., the range about 1 to about 5 includes 1, 1.5, 2, 2.75, 3, 3.80, 4, and 5, in increments of 0.0001) and any range within that range (e.g., the range of about 1.5 to about 3.78 within the range of 1 to 5, in increments of 0.0001).

Additional Embodiments

Condom Catheters:
1. A condom catheter 100 comprising: a cylindrical tubular member 10 sized to extend over a patient's penis (not shown) and having a first tubular member end 11, a second tubular member end 12 opposite said first tubular member end 11, a tubular member outer surface 13 extending between said first tubular member end 11 and said second tubular member end 12, a tubular member inner surface 14 extending between said first tubular member end 11 and said second tubular member end 12, a first opening 15 at said first tubular member end 11, a second opening 16 at said second tubular member end 12, a tubular member channel 21 extending along said tubular member inner surface 14 from said first tubular member end 11 to said second tubular member end 12, and a side wall port 17 positioned along said tubular member 10, said side wall port 17 having a first side port end 18 proximate said tubular member outer surface 13, a second side port end 19 opposite said first side port end 18, a side port outer surface 22 extending between said first side port end 18 and said second side port end 19, a side port inner surface 23 extending between said first side port end 18 and said second side port end 19, a first side port opening 24 at said first side port end 18 along said tubular member inner surface 14, a second side port opening 25 at said second side port end 19, and a side port channel 26 extending along said side port inner surface 23 extending between said first side port end 18 and said second side port end 19 so as to provide fluid communication between second side port opening 25 and tubular member channel 21.
2. The condom catheter 100 of embodiment 1, wherein said first tubular member 10 has a tubular member outer diameter $tm_o$ and a tubular member inner diameter $tm_i$, both of which are less than about 65 millimeters (mm)(or any value less than 65 mm, including 65.00 mm, in increments of 0.01 mm, e.g., 35.54 mm, or any range of values below 65 mm, including 65.00 mm, in increments of 0.01 mm, e.g., from about 32.44 mm to about 40.00 mm); and an overall length $tm_L$ of less than about 200 mm (or any value less than 200 mm, including 200.00 mm, in increments of 0.01 mm, e.g., 135.00 mm, or any range of values below 200 mm, including 200.00 mm, in increments of 0.01 mm, e.g., from about 30.40 mm to about 140.00 mm).
3. The condom catheter 100 of embodiment 1 or 2, wherein said first tubular member 10 has a tubular member outer diameter $tm_o$ ranging from about from about 6.0 mm to about 40.0 mm and a tubular member inner diameter $tm_i$ ranging from about from about 6.0 mm to about 40.0 mm; and an overall length $tm_L$ ranging from about from about 50 mm to about 200.0 mm.

Figure 7:
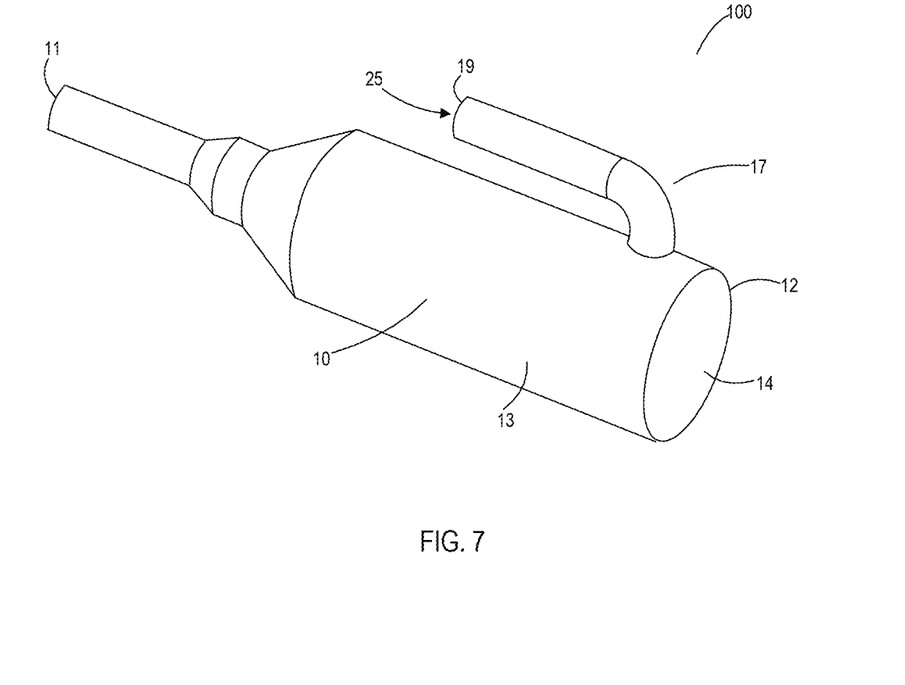
FIG. 7 depicts a view of another exemplary condom catheter of the present invention.
Figure 8:
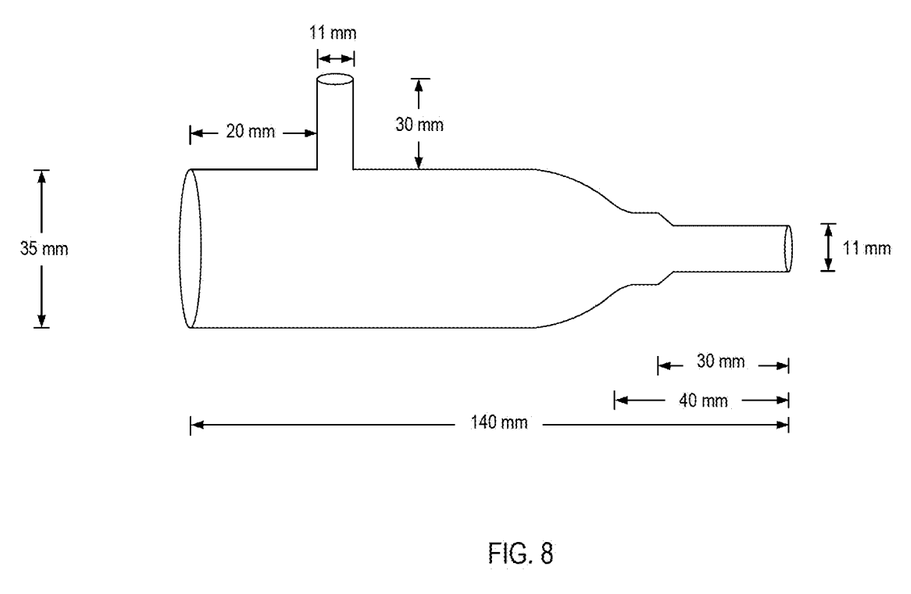
FIG. 8 depicts a view of another exemplary condom catheter of the present invention when exemplary dimensions shown.

4. The condom catheter 100 of embodiments 2 or 3, wherein both of said tubular member outer diameter $tm_o$ and said tubular member inner diameter $tm_i$ vary along overall length $tm_L$.
5. The condom catheter 100 of any one of embodiments 2 to 4, wherein said tubular member outer diameter $tm_o$ proximate said second tubular member end 12 ranges from about from about 120.0 mm to about 160.0 mm and said tubular member outer diameter $tm_o$ proximate said first tubular member end 11 ranges from about from about 6.0 mm to about 16.0 mm.
6. The condom catheter 100 of any one of embodiments 2 to 5, wherein said tubular member outer diameter $tm_o$ proximate said second tubular member end 12 is about 135.0 mm and said tubular member outer diameter $tm_o$ proximate said first tubular member end 11 is about 11.0 mm.
7. The condom catheter 100 of any one of embodiments 1 to 6, wherein said tubular member 10 comprises a first cylindrical portion 27 at said first tubular member end 11.
8. The condom catheter 100 of any one of embodiments 1 to 7, wherein said tubular member 10 comprises a second cylindrical portion 28 at said second tubular member end 12.
9. The condom catheter 100 of any one of embodiments 1 to 8, wherein said tubular member 10 comprises an intermediate tubular portion 29 between and connecting said first cylindrical portion 27 and said second cylindrical portion 28. In some embodiments, intermediate tubular portion 29 gradually decreases in cross-sectional area as intermediate tubular portion 29 moves from said second cylindrical portion 28 to said first cylindrical portion 27. In other embodiments, intermediate tubular portion 29 does not gradually decrease in cross-sectional area as intermediate tubular portion 29 moves from said second cylindrical portion 28 to said first cylindrical portion 27.
10. The condom catheter 100 of embodiment 9, wherein said intermediate tubular portion 29 has an outer diameter greater than an outer diameter of said first cylindrical portion 27 and less than an outer diameter of said second cylindrical portion 28.
11. The condom catheter 100 of any one of embodiments 1 to 10, wherein said side wall port 17 is closer to said second tubular member end 12 than said first tubular member end 11.
12. The condom catheter 100 of any one of embodiments 1 to 11, wherein said side wall port 17 is positioned a distance $d_{sp}$ from said second tubular member end 12.
13. The condom catheter 100 of embodiment 12, wherein said distance $d_{sp}$ ranges from about 10 mm to about 30 mm (or any value between 10 mm and 30 mm, including both endpoints 10 mm and 30 mm, in increments of 0.01 mm, e.g., 15.00 mm, or any range of values between 10 mm and 30 mm, including both endpoints 10 mm and 30 mm, in increments of 0.01 mm, e.g., from about 18.40 mm to about 20.50 mm).
14. The condom catheter 100 of any one of embodiments 1 to 14, wherein said side wall port 17 has a side port outer diameter $sp_o$ and a side port inner diameter $sp_i$, both of which are less than about 20 mm (or any value less than 20 mm, including 20.00 mm, in increments of 0.01 mm, e.g., 11.00 mm, or any range of values below 20 mm, including 20.00 mm, in increments of 0.01 mm, e.g., from about 12.44 mm to about 15.00 mm); and a side port length $sp_L$ ranging from about 10 mm to about 50 mm (or any value between 10 mm and 50 mm, including both endpoints 10 mm and 50 mm, in increments of 0.01 mm, e.g., 30.00 mm, or any range of values between 10 mm and 50 mm, including both endpoints 10 mm and 50 mm, in increments of 0.01 mm, e.g., from about 28.40 mm to about 30.50 mm).
15. The condom catheter 100 of embodiment 14, wherein said side port outer diameter $sp_o$ ranges from about from about 8.0 mm to about 12.0 mm, side port inner diameter $sp_i$ ranges from about from about 6.0 mm to about 12.0 mm; and said side port length $sp_L$ ranges from about from about 20.0 mm to about 40.0 mm.
16. The condom catheter 100 of any one of embodiments 1 to 15, wherein said side wall port 17 forms an angle A with said tubular member outer surface 13, said angle A ranging from about 0° (i.e., a portion of side wall port 17 extends in one direction, e.g., towards first end 11, along and is substantially parallel with said tubular member outer surface 13 as shown in FIG. 7) to about 180° (i.e., a portion of side wall port 17 extends in a direction opposite to that shown in in FIG. 7) (or any value between 0° and 180°, including both endpoints 0° and 180°, in increments of 0.1°, e.g., 90.0°, or any range of values between 0° and 180°, including both endpoints 0° and 180°, in increments of 0.1°, e.g., from about 15.0° to about 90.0°). Although not shown in the figures, side wall port 17 may have any configuration extending out from said tubular member outer surface 13, with any number of straight portions, curved portions, etc.
17. The condom catheter 100 of any one of embodiments 1 to 16, further comprising one or more additional side wall ports 17' positioned along said tubular member 10, each of said one or more additional side wall ports 17' having a first side wall port end 18' proximate said tubular member outer surface 13, a second side wall port end 19' opposite said first side wall port end 18', a side wall port outer surface 22' extending between said first side wall port end 18' and said second side wall port end 19', a side wall port inner surface 23' extending between said first side wall port end 18' and said second side wall port end 19', a first side wall port opening 24' at said first side wall port end 18' along said tubular member inner surface 14, a second side wall port opening 25' at said second side wall port end 19', and a side wall port channel 26' extending along said side wall port inner surface 23' extending between said first side wall port end 18' and said second side wall port end 19' so as to provide fluid communication between side wall port opening 25' and tubular member channel 21'. See, for example, additional side wall ports 17' shown in FIG. 13.
18. The condom catheter 100 of any one of embodiments 1 to 17, further comprising a release valve 55 positioned so as to open when a suction negative pressure exceeds a threshold amount. In some embodiments, the threshold amount is about 25 mm of mercury (Hg). See, for example, exemplary release valve 55 in FIG. 12.
19. The condom catheter 100 of embodiment 18, wherein said release valve 55 is positioned along one of said one or more additional side wall ports 17'. For example, the release valve 55 could be positioned at or proximate said second side wall port end 19' of one of said one or more additional side wall ports 17'.
20. The condom catheter 100 of embodiment 18, wherein said release valve 55 is positioned along said side wall port 17. For example, the release valve 55 could be positioned along said side wall port 17 at location 45 shown in FIG. 13.
21. The condom catheter 100 of any one of embodiments 1 to 20, wherein said tubular member outer surface 13 is separated from said tubular member inner surface 14 by a tubular member thickness $tm_t$ of less than about 3.0 mm (or any value between about 0.1 mm and 3.0 mm, including both endpoints 0.1 mm and 3.0 mm, in increments of 0.01 mm, e.g., 1.50 mm, or any range of values between about 0.1 mm and 3.0 mm, including both endpoints 0.1 mm and 3.0 mm, in increments of 0.01 mm, e.g., from about 1.40 mm to about 2.50 mm).

22. The condom catheter 100 of any one of embodiments 1 to 21, wherein said tubular member 10 and said side wall port 17 each independently comprise one or more condom catheter-forming materials. For example, any known condom catheter-forming material(s) may be used to form the condom catheters 100 of the present invention. Known materials include, but are not limited to, acrylics, latexes, silicones, nitrile, etc.

23. The condom catheter 100 of embodiment 22, wherein said one or more condom catheter-forming materials comprise a polymeric material.

24. The condom catheter 100 of embodiment 23, wherein said one or more condom catheter-forming materials further comprise a fibrous reinforcement material. Fibrous reinforcement materials may comprise any fiber-containing material including, but not limited to, a woven fabric/scrim/mesh, a nonwoven fabric, unidirectional fibers, a knitted fabric, strands of fibers, or any combination thereof. Further, fibrous materials may comprise any type of fiber including but not limited to, fiberglass fibers, polymeric fibers (e.g., nylon), elastomeric fibers, aramid fibers, ceramic fibers, cellulosic fibers (e.g., cotton), or any combination thereof.

25. The condom catheter 100 of any one of embodiments 22 to 25, wherein said one or more condom catheter-forming materials comprise a 3D printable material.

Figure 3:
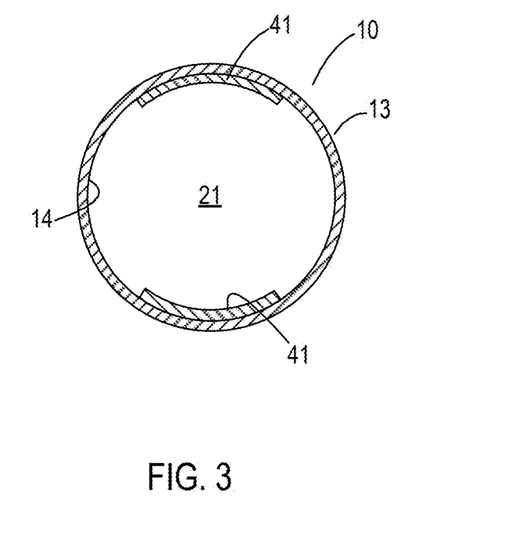
FIG. 3 depicts a cross-sectional view of the exemplary condom catheter shown in FIG. 2 along view 3-3 shown in FIG. 2.
Figure 4:
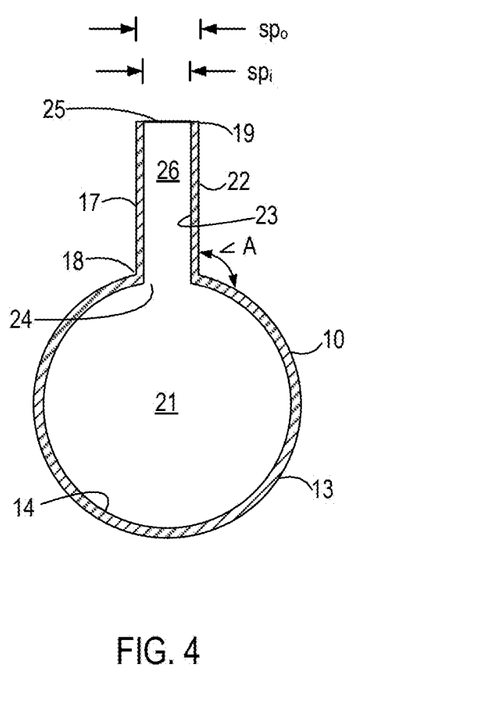
FIG. 4 depicts a cross-sectional view of the exemplary condom catheter shown in FIG. 2 along view 4-4 shown in FIG. 2.
Figure 5:
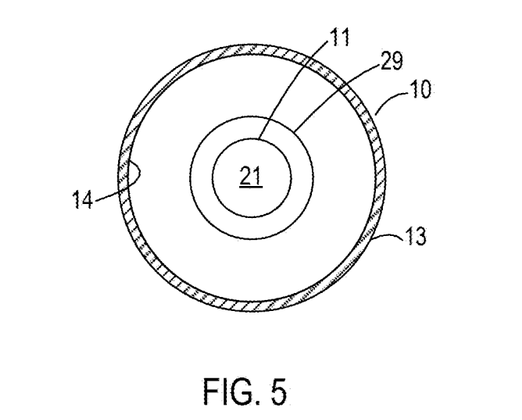
FIG. 5 depicts a cross-sectional view of the exemplary condom catheter shown in FIG. 2 along view 5-5 shown in FIG. 2.
Figure 6:
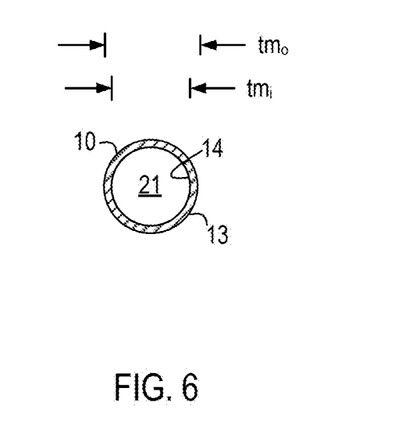
FIG. 6 depicts a cross-sectional view of the exemplary condom catheter shown in FIG. 2 along view 6-6 shown in FIG. 2.

26. The condom catheter 100 of any one of embodiments 1 to 25, further comprising one or more areas of adhesive 41 positioned along said tubular member inner surface 14. See, for example, areas of adhesive 41 shown in FIG. 3.

Figure 14:
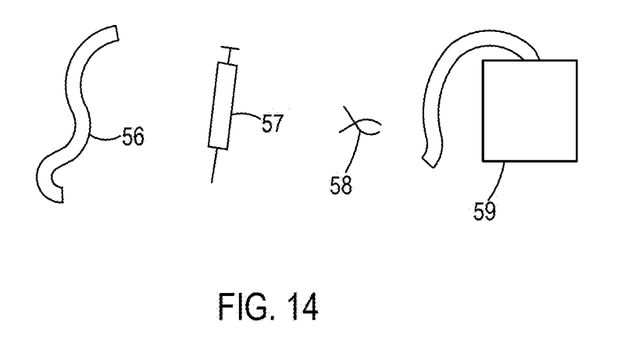
FIG. 14 depicts a view of exemplary kit components suitable for use with the exemplary condom catheters of the present invention.

Kits Comprising Condom Catheters:

27. A kit comprising the condom catheter 100 of any one of embodiments 1 to 26 and one or more additional kit components, some of which are shown in FIG. 14.

Figure 9:
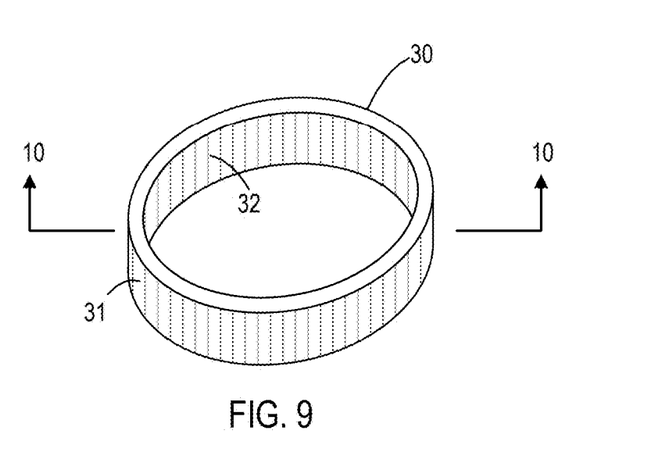
FIG. 9 depicts a view of an exemplary sponge ring that may be used with the condom catheters of the present invention.
Figure 10:
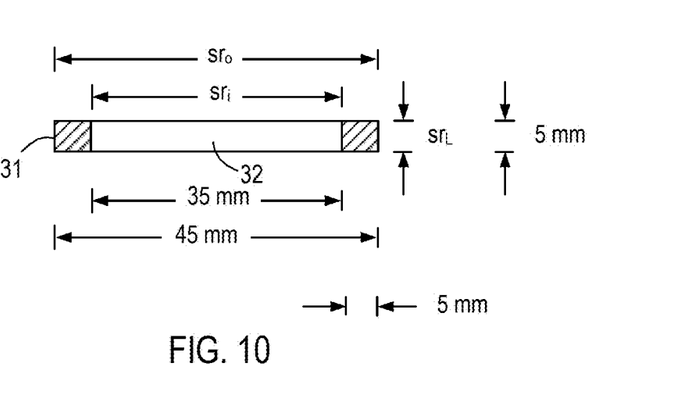
FIG. 10 depicts a cross-sectional view of the exemplary sponge ring shown in FIG. 9 along view 10-10 shown in FIG. 9.
Figure 11:
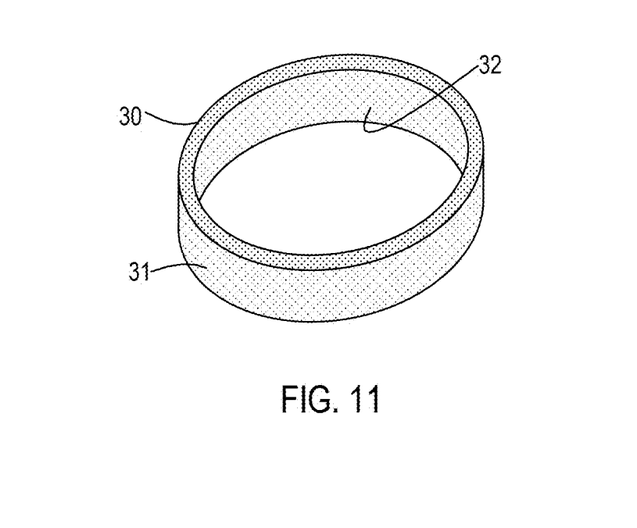
FIG. 11 depicts a view of another exemplary sponge ring that may be used with the condom catheters of the present invention.

28. The kit of embodiment 27, wherein said one or more additional kit components comprise at least one open cell sponge ring 30 sized to be positionable within said cylindrical tubular member 10. See exemplary open cell sponge ring 30 shown in FIGS. 9-11 and shown in use in FIG. 12. As shown in FIGS. 9-11, sponge ring 30 has a sponge ring outer surface 31, and a sponge ring inner surface 32. Desirably, sponge ring 30 has dimensions such that, when positioned within said cylindrical tubular member 10, sponge ring outer surface 31 is positioned along said tubular member inner surface 14 of said cylindrical tubular member 10, and sponge ring inner surface 32 is positioned along a patient's penis (not shown). See, for example, the position of exemplary open cell sponge ring 30 shown in use in FIG. 12.

29. The kit of embodiment 28, wherein said at least one open cell sponge ring 30 has a sponge ring outer diameter $sr_o$ and a sponge ring inner diameter $sr_i$, both of which are less than about 65 mm (or any value less than 65 mm, including 65.00 mm, in increments of 0.01 mm, e.g., 35.54 mm, or any range of values below 65 mm, including 65.00 mm, in increments of 0.01 mm, e.g., from about 32.44 mm to about 40.00 mm); and an overall sponge ring length $sr_L$ of less than about 20 mm (or any value less than 20 mm, including 20.00 mm, in increments of 0.01 mm, e.g., 5.00 mm, or any range of values below 20 mm, including 20.00 mm, in increments of 0.01 mm, e.g., from about 3.40 mm to about 4.00 mm).

30. The kit of embodiment 28 or 29, wherein said at least one open cell sponge ring 30 is positioned within said cylindrical tubular member 10.

Figure 12:
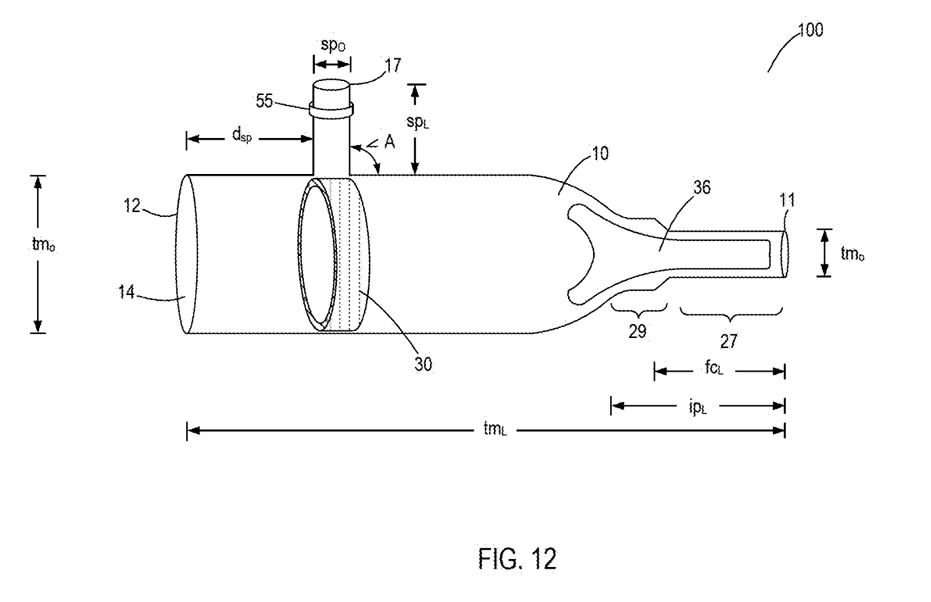
FIG. 12 depicts a view of the exemplary condom catheter shown in FIGS. 1-2 with the exemplary sponge ring of FIG. 11 positioned within the exemplary condom catheter.
Figure 13:
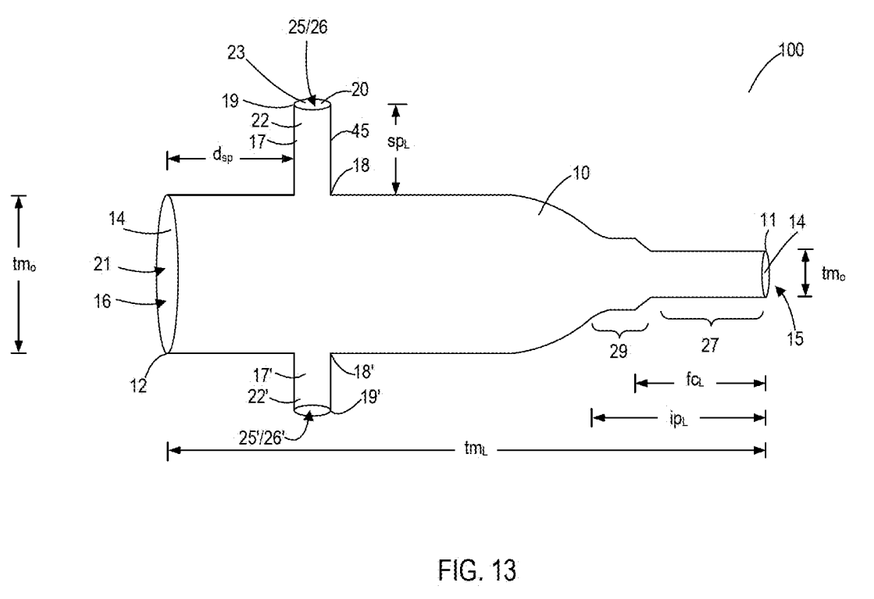
FIG. 13 depicts a view of another exemplary condom catheter of the present invention.

31. The kit of any one of embodiments 27 to 30, wherein said one or more additional kit components comprise at least one open cell sponge end piece 36 sized to be positionable within said cylindrical tubular member 10. See exemplary open cell sponge end piece 36 shown in use in FIG. 12. Open cell sponge end piece 36 may be used as shown in FIG. 12 to prevent collapse of side walls of tubular member 27 (e.g., side walls of at least a portion of (i) first cylindrical portion 27 and/or (ii) intermediate tubular portion 29 and/or (iii) second cylindrical portion 28 at first tubular member end 11) when suction is applied to first opening 15 at first tubular member end 11, allowing suction of urine and fixation of the condom catheter wall to the penile shaft as an alternative to the side port suction.

32. The kit of any one of embodiments 27 to 31, wherein said one or more additional kit components comprise plastic tubing 56 sized to connect to said side wall port 17 and/or said one or more additional side wall ports 17' and/or said first tubular member end 11 of said cylindrical tubular member 10. See, exemplary plastic tubing 56 shown in FIG. 14.

33. The kit of any one of embodiments 27 to 32, wherein said one or more additional kit components comprise one or more of: a syringe 57, a release valve 55, a clamp 58, and a suction-providing system 59. Suction-providing devices 59 include, but are not limited to, an electric wall intermittent suction 59, a portable battery operated suction 59 (as used in wound vacuum procedures), a spring loaded syringe 57 or regular syringe 57 and one way valve.

Methods of Making a Condom Catheter:

34. A method of making the condom catheter 100 of any one of embodiments 1 to 26, said method comprising: forming the tubular member 10 and the side wall port 17.

35. The method of embodiment 34, wherein the tubular member 10 and the side wall port 17 are integrally formed with one another.

36. The method of embodiment 34 or 35, wherein said forming step comprises a thermoforming step (e.g., molding, injection molding, blow molding, dip molding, heat stamping or ultrasonic welding, etc.).

37. The method of any one of embodiments 34 to 36, wherein said forming step further comprises forming the one or more additional side wall ports 17'.

Methods of Using Condom Catheters:

38. A method of using the condom catheter 100 of any one of embodiments 1 to 26, said method comprising: positioning the condom catheter 100 on a patient; and applying suction through the side wall port 17 so as to increase a bonding strength between the condom catheter 100 and the patient.

39. A method of using the condom catheter 100 of any one of embodiments 1 to 26, said method comprising: securing the condom catheter 100 to a patient by applying a suction force through the side wall port 17 so as to increase a bonding strength between the condom catheter 100 and the patient.

40. The method of embodiment 38 or 39, wherein said applying step comprises attaching the side wall port 17 to a suction-providing system 59. The suction-providing system 59 may be in an operating room setting or may be at a patient's home, a nursing home, a regular hospital bed or an ICU bed. As discussed above, the suction-providing device 59 may comprise an electric wall intermittent suction 59, a portable battery operated suction 59 (as used in wound vacuum procedures), a spring loaded syringe 57 or regular syringe 57 and one way valve.

41. The method of any one of embodiments 38 to 40, wherein said applying step comprises attaching the side wall port 17 to a syringe 57 and created suction via the syringe 57.
42. The method of any one of embodiments 38 to 41, further comprising positioning the at least one open cell sponge ring 30 within the cylindrical tubular member 10 prior to said applying step.
43. The method of any one of embodiments 38 to 42, further comprising positioning the at least one open cell end piece 36 within the cylindrical tubular member 10 prior to said applying step.
44. The method of any one of embodiments 38 to 43, wherein said applying step creates up to about negative 25 mm of Hg suction pressure to bond the condom catheter to the patient.
45. The method of any one of embodiments 38 to 44, wherein if during said applying step a suction pressure exceeds about negative 25 mm of Hg, a release valve 55 opens so as to reduce the suction pressure within the condom catheter.

It should be understood that although the above-described condom catheters, and methods are described as "comprising" one or more components or steps, the above-described condom catheters, kits, and methods may "comprise," "consists of," or "consist essentially of" any of the above-described components or steps of the condom catheters, kits, and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a condom catheter, a kit, and/or a method that "comprises" a list of elements (e.g., components or steps) is not necessarily limited to only those elements (or components or steps), but may include other elements (or components or steps) not expressly listed or inherent to the condom catheter, the kit, and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define condom catheters, and methods that include materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described condom catheters, kits, and methods may comprise, consist essentially of, or consist of any of the herein-described components and features, as shown in the figures with or without any feature(s) not shown in the figures. In other words, in some embodiments, the condom catheters, kits, and/or methods of the present invention do not have any additional features other than those shown in the figures, and such additional features, not shown in the figures, are specifically excluded from the condom catheters, kits, and/or methods. In other embodiments, the condom catheters, kits, and/or methods of the present invention do have one or more additional features that are not shown in the figures.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of Condom Catheters

Exemplary Condom Catheters as Shown in FIGS. 1-13 Were Prepared

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:
1. A condom catheter kit comprising:
 a condom catheter comprising:
  a cylindrical tubular member sized to extend over a patient's penis and having a first tubular member end, a second tubular member end opposite said first tubular member end, a tubular member outer surface extending between said first tubular member end and said second tubular member end, a tubular member inner surface extending between said first tubular member end and said second tubular member end, a first opening at said first tubular member end, a second opening at said second tubular member end, a tubular member channel extending along said tubular member inner surface from said first tubular member end to said second tubular member end; and
  a side wall port positioned along said tubular member, said side wall port having a first side port end proximate said tubular member outer surface, a second side port end opposite said first side port end, a side port outer surface extending between said first side port end and said second side port end, a side port inner surface extending between said first side port end and said second side port end, a first side port opening at said first side port end along said tubular member inner surface, a second side port opening at said second side port end, and a side port channel extending along said side port inner surface extending between said first side port end and said second side port end so as to provide fluid communication between second side port opening and tubular member channel; and at least one open cell sponge, continuous closed ring sized to be positionable within said cylindrical tubular member, said at least one open cell sponge, continuous closed ring, when positioned within said cylindrical tubular member, is positioned such that a sponge ring outer surface is positioned along said tubular member inner surface of said cylindrical tubular member, and a sponge ring inner surface is positioned along a patient's penis; and a suction-providing system configured to deliver suction through the side wall port so as to increase a bonding strength between the condom catheter and the patient's penis.

2. The condom catheter kit of claim 1, wherein said first tubular member has a tubular member outer diameter $tm_o$ ranging from about from about 6.0 mm to about 40.0 mm; a tubular member inner diameter $tm_i$ ranging from about from about 6.0 mm to about 40.0 mm; and an overall length $tm_L$ ranging from about from about 50.0 mm to about 200.0 mm.

3. The condom catheter kit of claim 2, wherein both of said tubular member outer diameter $tm_o$ and said tubular member inner diameter $tm_i$ vary along overall length $tm_L$.

4. The condom catheter kit of claim 2, wherein said tubular member outer diameter $tm_o$ proximate said second tubular member end ranges from about from about 120.0 mm to about 160.0 mm and said tubular member outer diameter $tm_o$ proximate said first tubular member end ranges from about from about 6.0 mm to about 16.0 mm.

5. The condom catheter kit of claim 2, wherein said tubular member outer diameter $tm_o$ proximate said second tubular member end is about 135.0 mm and said tubular member outer diameter $tm_o$ proximate said first tubular member end is about 11.0 mm.

6. The condom catheter kit of claim 1, wherein said tubular member comprises a first cylindrical portion at said first tubular member end, a second cylindrical portion at said second tubular member end, and an intermediate tubular portion between and connecting said first cylindrical portion and said second cylindrical portion.

7. The condom catheter kit of claim 6, wherein said intermediate tubular portion has an outer diameter greater than an outer diameter of said first cylindrical portion and less than an outer diameter of said second cylindrical portion.

8. The condom catheter kit of claim 1, wherein said side wall port is closer to said second tubular member end than said first tubular member end.

9. The condom catheter kit of claim 1, wherein said side wall port is positioned a distance $d_{sp}$ from said second tubular member end, wherein said distance $d_{sp}$ ranges from about 10 mm to about 30 mm.

10. The condom catheter kit of claim 1, wherein said side wall port has a side port outer diameter $sp_o$ and a side port inner diameter $sp_i$, both of which are less than about 20 mm; and a side port length $sp_L$ ranging from about 10 mm to about 50 mm.

11. The condom catheter kit of claim 1, wherein said side wall port forms an angle A with said tubular member outer surface, said angle A ranging from about 0° to about 180°.

12. The condom catheter kit of claim 1, further comprising one or more additional side wall ports positioned along said tubular member, each of said one or more additional side wall ports having a first side wall port end proximate said tubular member outer surface, a second side wall port end opposite said first side wall port end, a side wall port outer surface extending between said first side wall port end and said second side wall port end, a side wall port inner surface extending between said first side wall port end and said second side wall port end, a first side wall port opening at said first side wall port end along said tubular member inner surface, a second side wall port opening at said second side wall port end, and a side wall port channel extending along said side wall port inner surface extending between said first side wall port end and said second side wall port end so as to provide fluid communication between side wall port opening and tubular member channel.

13. The condom catheter kit of claim 1, further comprising a release valve positioned so as to open when a suction negative pressure exceeds a threshold amount, wherein said release valve is positioned along said side wall port.

14. The condom catheter kit of claim 1, wherein said tubular member outer surface is separated from said tubular member inner surface by a tubular member thickness $tm_t$ of less than about 3.0 mm.

15. The condom catheter kit of claim 1, wherein said tubular member and said side wall port each independently comprise one or more condom catheter-forming materials, wherein said one or more condom catheter-forming materials comprise a polymeric material, a fibrous reinforcement material, a 3D printable material, or any combination thereof.

16. The condom catheter kit of claim 1, further comprising one or more areas of adhesive positioned along said tubular member inner surface.

17. The condom catheter kit of claim 1, further comprising one or more additional kit components, wherein said one or more additional kit components comprise (i) at least one open cell sponge end piece sized to be positionable within said cylindrical tubular member, (ii) plastic tubing sized to connect to said side wall port and/or said first tubular member end of said cylindrical tubular member, (iii) a syringe, (iv) a release valve, and (v) a clamp.

18. The condom catheter kit of claim 1, wherein said at least one open cell sponge, continuous closed ring has a sponge ring outer diameter $sr_o$ and a sponge ring inner diameter $sr_i$, both of which are less than about 65 mm; and an overall sponge ring length $sr_L$ of less than about 20 mm.

19. A method of using a condom catheter kit, said method comprising:

positioning at least one open cell sponge, continuous closed ring onto a patient's penis;

positioning a condom catheter over the patient's penis and the at least one open cell sponge, continuous closed ring, the condom catheter comprising:

a cylindrical tubular member sized to extend over the patient's penis and having a first tubular member end, a second tubular member end opposite the first tubular member end, a tubular member outer surface extending between the first tubular member end and the second tubular member end, a tubular member inner surface extending between the first tubular member end and the second tubular member end, a first opening at the first tubular member end, a second opening at the second tubular member end, a tubular member channel extending along the tubular member inner surface from the first tubular member end to the second tubular member end: and a side wall port positioned along the tubular member, the side wall port having a first side port end proximate the tubular member outer surface, a second side port end opposite the first side port end, a side port outer surface extending between the first side port end and the second side port end, a side port inner surface extending between the first side port end and the second side port end, a first side port opening at the first side port end along the tubular member inner surface, a second side port opening at the second side port end, and a side port channel extending along the side port inner surface extending between the first side port end and the second side port end so as to provide fluid communication between second side port opening and tubular member channel; and applying suction through the side wall port so as to increase a bonding strength between the condom catheter and the patient's penis.

\* \* \* \* \*